United States Patent
Yliollitervo et al.

(10) Patent No.: US 10,736,772 B2
(45) Date of Patent: Aug. 11, 2020

(54) FLUID CIRCULATION SYSTEM FOR A CRYOCABIN ARRANGEMENT AND RELATED CRYOCABIN ARRANGEMENT

(71) Applicant: CRYOTECH NORDIC OU, Vaana, Harjumaa, Tallinn (EE)

(72) Inventors: Juha Tapani Yliollitervo, Jarvenpaa (FI); Jan Eklund, Vantaa (FI); Jean-Patric Martins, Tallinn (EE)

(73) Assignee: CRYOTECH NORDIC OU, Vaana, Harjumaa (EE)

( * ) Notice: Subject to any disclaimer, the term of this patent is extended or adjusted under 35 U.S.C. 154(b) by 573 days.

(21) Appl. No.: 15/410,075

(22) Filed: Jan. 19, 2017

(65) Prior Publication Data

US 2017/0209302 A1 Jul. 27, 2017

(30) Foreign Application Priority Data

Jan. 19, 2016 (FI) .................................. 20165030

(51) Int. Cl.
*A61F 7/00* (2006.01)
*F25D 3/10* (2006.01)

(52) U.S. Cl.
CPC .............. *A61F 7/0053* (2013.01); *F25D 3/10* (2013.01); *A61F 2007/0064* (2013.01); *A61F 2007/0095* (2013.01)

(58) Field of Classification Search
CPC ............ A61F 7/0053; A61F 2007/0054; A61F 2007/0056; A61F 2007/0057; A61F 2007/0059; A61F 2007/0063; A61F 2007/0064; A61F 7/0085; A61F 2007/0095; A61F 2007/0096

USPC ....................................................... 607/81–87
See application file for complete search history.

(56) References Cited

U.S. PATENT DOCUMENTS

| | | | |
|---|---|---|---|
| 4,698,976 A * | 10/1987 | Fieseler ................ | A61F 7/0085 62/46.1 |
| 4,784,140 A | 11/1988 | Donnerhack et al. | |
| 4,838,270 A | 6/1989 | Donnerhack et al. | |
| 4,880,003 A * | 11/1989 | Donnerhack ......... | A61F 7/0053 607/83 |

(Continued)

FOREIGN PATENT DOCUMENTS

| | | |
|---|---|---|
| EP | 0226107 A1 | 6/1987 |
| FR | 2981268 A1 | 4/2013 |

OTHER PUBLICATIONS

Finnish Search Report, dated Aug. 18, 2016, from corresponding Finnish Application.

*Primary Examiner* — Ahmed M Farah
(74) *Attorney, Agent, or Firm* — Young & Thompson (57) ABSTRACT

The invention concerns a fluid circulation and mixing system (100) for a cryocabin arrangement used in a whole-body cryotherapy treatment and a related cryocabin arrangement (120), including a system (100) and a cabin (101) for accommodating a patient. The fluid circulation system (100) includes appliances for effective mixing of cryogenic liquid with ambient air and/or for preventing the cryogenic liquid from settling down on the bottom of evaporator. The cryocabin arrangement (120) further includes appliances for generating and maintaining a fluidic whirl (vortex) within the patient cabin, thus enhancing an overall efficiency of the cryotherapy treatment in general and improving beneficial effects of each individual cryotherapy treatment session.

7 Claims, 5 Drawing Sheets

(56) References Cited

U.S. PATENT DOCUMENTS

| | | | |
|---|---|---|---|
| 8,162,930 B2 * | 4/2012 | Brojek | A61F 7/0053 606/20 |
| 10,271,986 B1 * | 4/2019 | Guertin | A61F 7/0053 |
| 2007/0293920 A1 * | 12/2007 | Brojek | A61F 7/0053 607/104 |
| 2013/0025302 A1 * | 1/2013 | Lyubchenko | A61F 7/0053 62/89 |
| 2017/0007443 A1 * | 1/2017 | Stroze | A61F 7/0053 |

\* cited by examiner

FLUID CIRCULATION SYSTEM FOR A CRYOCABIN ARRANGEMENT AND RELATED CRYOCABIN ARRANGEMENT

FIELD OF THE INVENTION

The present invention generally relates to cryogenic devices for carrying out cryotherapy on the entire body of a patient; more particularly, the invention concerns a fluid circulation and mixing system for a cryocabin arrangement and a related cryocabin arrangement.

BACKGROUND

Cryotherapy as a whole-body cold therapy is a promising method for enhancing general well-being of an individual, including treatment and prevention of depression and fatigue, as well as for invoking and/or reactivating internal resources of the organism, thus promoting its natural capacity for a self-defense against various diseases including asthma, hormone deficiencies, joint inflammation and skin disorders, such as allergies and psoriasis. Upon exposing the patient's skin to an impact of the extreme temperatures, such as below −100 degrees Celsius (typically within a range of −110 to −170° C.), for 1-3 minutes at a time, the body develops stress response, followed by activation of metabolic processes, acceleration and intensification of blood circulation, increased oxygen supply to cells and tissues and release of anti-inflammatory and analgesic substances, that altogether results in an at least alleviation of pain, reduced swelling and diminished muscle tension. Long-term effects of cryotherapy thus include an enhanced immune resistance of the organism and an improved flexibility and elasticity of soft tissues and skin. Extreme cold also promotes cell replacement processes naturally occurring within the body, and elimination of dead cells, accordingly.

In this regard, whole-body cryotherapy is particularly effective for use in cosmetic treatment, as for preventing and/or delaying ageing processes, for example. Additionally, whole-body cryotherapy can be successfully utilized for promoting healing after surgery, as well as for retaining good physical shape and accelerating restoration after intensive physical training and/or sport competitions.

Devices for carrying out the whole-body cryotherapy are known from the art. Thus, the U.S. Pat. No. 8,162,930 (Brojek) discloses a cryogenic chamber and a cryogenic cabin with means for producing a low temperature (−60 to −160° C.) therewithin by vaporizing liquefied gas(es) to create a cold breathable atmosphere in the chamber. In its preferred implementation the cryogenic cabin is situated inside the chamber, so that the closed cabin comprises an air intake device for providing breathing air to the patient. The U.S. Pat. No. 4,838,270 (Donnerhack et al) discloses, in turn, a walk-in cryogenic cabin in the form of a half-shell open at the top. In the aforesaid publications supply of the cold treatment gas is implemented via a heat exchanger.

Another kind of walk-in devices for carrying out the whole-body cryotherapy is known as cryosauna and is based on a direct supply of cold treatment gas into the treatment cabin accommodating a patient. Such cryosauna devices are equipped with a gas mixing unit, allowing mixing of coolant (liquefied gas) with ambient air, and supplying the resulting mix into the treatment cabin. Thus, the United States patent application No. 2013/0025302 (Lyubchenko) discloses a cryosauna comprising the aforementioned gas mixing unit (gas generator) which in turn comprises an evaporation tank for self-evaporating liquefied gas/cooling agent and a mixer for mixing the evaporated cooling agent with an ambient air, after that a mixture of the self-evaporated cooling agent and air is directed into the treatment cabin.

However, the abovementioned cryosauna device and/or other devices for a whole-body cryotherapy are constrained with common technical problems. The first problem concerns, in particular, the so-called cryosauna devices enabling direct supply of coolant mix into the treatment cabin. Thus, when the cooling agent, such as liquefied gas, is supplied into the gas mixing unit, it is allowed to evaporate therein largely by itself (self-evaporation). However, once supplied into the gas mixing unit said cooling agent normally tends to re-acquire a liquid state at the bottom of the evaporation tank, which in practice leads to a situation when an amount of cooling energy, potentially releasable from said cooling agent, drastically decreases, since considerable amount of the cooling agent could not be effectively exploited/delivered to the patient chamber. Auxiliary appliances for promoting self-evaporation of the cooling agent, such as a duct fan, described in the US 2013/0025302, are clearly not sufficient to promote and/or intensify evaporation of liquefied gas within the gas mixing unit. Another problem, concerning in general all existing devices for the whole-body cryotherapy, is an absence or insufficiency of cold fluid circulation within the treatment (patient) cabin. Therefore, room for improvement exists with regard the at least above mentioned issues.

SUMMARY OF THE INVENTION

An objective of the present invention is to at least alleviate one or more problems arising from the limitations and disadvantages of the related art. The objective is achieved by various embodiments of a fluid circulation system for a cryocabin arrangement with direct supply of cooling fluid thereto and a related cryocabin arrangement.

Thereby, in one aspect of the invention a fluid circulation system for a cryocabin used in a whole-body cryotherapy treatment and configured to supply a cooling agent directly into said cryocabin is provided, said fluid circulation system comprises a volatilization tank and a mixing tank being in fluid communication with each other and with the cryocabin, said fluid circulation system further comprises a cryogenic liquid intake appliance for supply of cryogenic liquid into the volatilization tank and a compressed air intake appliance for supply of compressed air into the volatilization tank, which appliances are disposed adjacent to each other, said fluid circulation system being further configured for a compressed air intake into the volatilization tank in regular periodic pulses during the course of the cryotherapy treatment session.

In one preferred embodiment the fluid circulation system is configured such that the compressed air intake appliance is disposed below the cryogenic liquid intake appliance. In some preferred embodiment the fluid circulation system is further configured such that the intake of compressed air into the volatilization tank is controlled by a computer-regulated valve, preferably a solenoid valve.

In some embodiment the fluid circulation system is configured to direct a mixture of cryogenic liquid supplied via the cryogenic liquid intake appliance and air supplied via the compressed air intake appliance from the volatilization tank to the mixing tank via a pipe arrangement by means of an impeller arrangement.

In some preferred embodiment the fluid circulation system is configured such, that cryogenic liquid supplied thereto is a mixture of liquid nitrogen and liquid oxygen, wherein the content of liquid oxygen in said mixture is within a range of 19-21%.

The fluid circulation system is advantageously configured to direct the cooling agent into the cryocabin via the mixing tank and to receive a discharge fluid from the cryocabin into the volatilization tank. The fluid circulation system is further configured to supply into the cryocabin a cooling agent comprising volatilized cryogenic liquid and ambient air.

In another aspect a cryocabin arrangement for use in a whole-body cryotherapy treatment is provided, comprising a vertical open-top cabin for accommodating a patient and a fluid circulation system configured to supply a cooling agent directly into the patient cabin, which fluid circulation system being implemented according to the previous aspect of the invention, wherein the patient cabin comprises a cooling agent intake appliance and a fluid discharge appliance disposed at the upper half of said cabin adjacent to each other, wherein the patient cabin further comprises a compressed air intake appliance disposed at the bottom part thereof, said appliance being configured to generate a diagonally ascending airstream, and wherein the cryocabin arrangement is further configured for a compressed air intake into the cabin in regular periodic pulses during the course of the cryotherapy treatment session.

In one preferred embodiment the cryocabin arrangement is configured such that the intake of compressed air into the patient cabin is controlled by computer-regulated valve, preferably a solenoid valve.

In some preferred embodiment provision of the cryocabin arrangement is such that the compressed air intake appliance within the patient cabin is configured to generate an air stream along a trajectory forming an inclination angle with an imaginary line corresponding to the bottom of the patient cabin, said angle being less than 90°, preferably within a range of 5° to 60°. Furthermore, the cryocabin arrangement is preferably configured, upon supply of the cooling agent —and compressed air streams into the patient cabin, to generate and maintain, during the course of the cryotherapy treatment session, a fluidic whirl created upon interaction of aforesaid fluidic streams having distinct direction and temperature.

In some embodiment the cryocabin arrangement is further configured to maintain the temperature inside the patient cabin within a range of −100 to −180 degrees Celsius.

In still further embodiment the cryocabin arrangement comprises an at least one thermographic camera integrated within the patient cabin provided with said arrangement, the thermographic camera being configured for a real-time monitoring the body temperature of the patient during the course of the cryotherapy treatment session.

The utility of the present invention arises from a variety of reasons depending on embodiments thereof. At first, the fluid circulation system for a cryocabin arrangement disclosed hereby allows for effective exploitation of all cryogenic liquid (liquefied gas) once supplied into said system by provision of compressed air delivery means directly into a cryogenic liquid volatilization tank. In practice this means that all cryogenic liquid once supplied into the fluid circulation system is efficiently volatilized and used for cooling a patient cabin. Such effective exploitation contributes to reducing an amount of cryogenic liquid required for a single cryotherapy session. As a consequence, overall energy consumption of the entire cryogenic cabin installation decreases, improving operating efficiency thereof.

Moreover, efficient redistribution of a cooling agent within the cryocabin arrangement disclosed hereby and generation of a fluidic whirl (substantially circular flow, vortex) in the patient cabin allow for cooling said cabin down to the temperatures in a range of −100 to −180 degrees Celsius (° C.) within a time period of 30-120 seconds, thus enhancing an overall efficiency of the cryotherapy treatment in general and improving beneficial effects of each individual cryotherapy treatment session.

The term "cryosauna" indicates in the present disclosure a cryocabin arrangement with a direct cooling system, in which a gaseous cooling agent, provided as a mixture of cryogenic liquid with ambient air, is supplied directly into the patient cabin.

The term "volatilization" indicates in the present disclosure generation of vapors occurring upon supply of the cooling agent from the cooling agent source to the volatilization tank due to the ambient heat. The terms "evaporation" and "boil-off" are used as synonyms to the "volatilization", accordingly.

The term "cryogenic liquid" is used herewith to indicate liquefied gas supplied from an appropriate cryogenic liquid source.

The expression "a number of" refers herein to any positive integer starting from one (1), e.g. to one, two, or three.

The terms "first" and "second" are used herein to distinguish an element from another element and not to denote any particular order or importance if not otherwise explicitly indicated.

The term "element" may herein refer also to a multi-part element with multiple functionally and optionally also physically connected elements in addition to single-part or integrated elements.

Different embodiments of the present invention will become apparent by consideration of the detailed description and accompanying drawings.

DETAILED DESCRIPTION OF THE EMBODIMENTS

Detailed embodiments of the present invention are disclosed herein with the reference to accompanying drawings. The same reference characters are used throughout the drawings to refer to same members. Following citations are used for the members:

100—a fluid circulation system;
10, 10a—a compressed air intake appliance (for system 100);
11—a control valve for the appliance 10, 10a;
12, 12a—a cryogenic liquid intake appliance;
13—a volatilization tank;
14, 14a—a fluid intake pipe and a fluid stream therein;
15—an impeller arrangement;

16, 16a—a fluid return pipe and a fluid stream therein;
17—a mixing tank;
18, 18a—an outlet for a cooling agent directed from the fluid circulation system into a patient cabin, and a cooling agent stream therein (system 100);
19, 19a—an inlet for discharge fluid returned from the patient cabin back into the fluid circulation system, and a discharge fluid stream therein (system 100);
20—a casing;
20a, 20b—front and back panels of the casing, accordingly;
101—a cabin for accommodating a patient;
110, 110a—a compressed air intake appliance (for the cabin 101);
111—a control valve for the appliance 110, 110a;
114—a diagonally ascending airstream;
115—a fluidic whirl (vortex);
118—an intake appliance for the cooling agent directed from the fluid circulation system (cabin 101);
119—a fluid discharge appliance (cabin 101);
120—a cryocabin arrangement;
121—a base;
122—a door;
123—an interspace between the base and a patient platform;
124—a standing platform for accommodating a patient;
125—protection shields;
126—an illumination and sensor appliance;
127, 128—parameter screens;
129—a control terminal.

Figure 1:
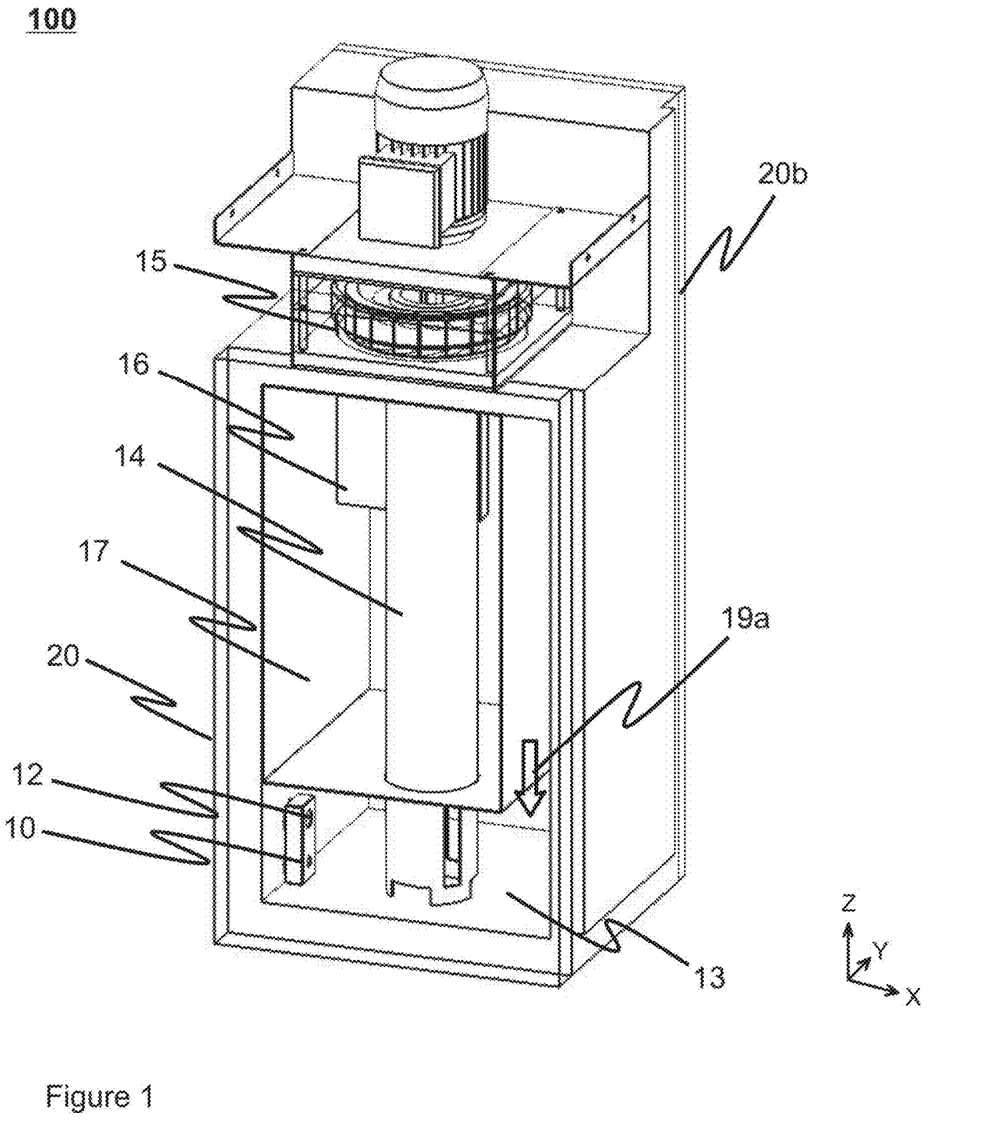
FIG. 1 is a perspective view of a fluid circulation system in accordance with one aspect of the invention.

FIG. 1 illustrates at 100 the concept underlying various embodiments of a fluid circulation system of the present invention. The system 100 is suitable for a cryocabin used in a whole-body cryotherapy treatment and is configured to supply a cooling agent directly into said cryocabin. Provision of the system 100 allows for an effective mixing of liquefied gas(es) with ambient air therewithin and for further directing the resulting cooling agent into the cabin accommodating a patient.

The system 100 generally comprises a volatilization tank 13 and a mixing tank 17 provided within a casing 20. The mixing tank 17 is preferably provided as a separate container positioned within the casing 20 such that the space occupied by the volatilization tank 13 forms an L-shape. The casing 20, the volatilization tank 13 and the mixing tank 17 are heat-insulated.

Fluid intake inside the system 100 is implemented via fluid supply ports 10 and 12 provided in the casing 20 and corresponding fluid supply lines 10a, 12a (FIG. 3) connected thereto. In preferred embodiment the system 100 has provisions for intake each of cryogenic liquid and compressed air. Thus, cryogenic liquid is supplied into the system 100 via the port 12 and the line 12a; whereas compressed air is supplied via the port 10 and the line 10a, said ports 10 and 12 being disposed adjacent to each other. The port 10 and the line 10a thus form a compressed air intake appliance 10, 10a, and the port 12 and the line 12a form a cryogenic liquid intake appliance 12, 12a, accordingly. As seen from FIGS. 1 and 3, the appliances 10, 10a and 12, 12a are disposed on a side wall of the casing 20 adjacent to each other. In the particularly preferred embodiment the compressed air intake appliance 10, 10a is disposed below the cryogenic liquid intake appliance 12, 12a for the reasons explained further below. Intake of compressed air into the volatilization tank 13 is further controlled by a computer-regulated valve 11, preferably implemented as a solenoid valve, said valve 11 provided at the supply line 10a.

The cryogenic liquid is preferably a mixture of liquefied gases, namely of nitrogen and oxygen in a percent ratio of approximately 80 to 20. Oxygen content in the aforesaid mixture is preferably 19-21%. However, utilization of liquid nitrogen, liquid air and/or other appropriate cryogenic liquid is not excluded. Intake of cryogenic liquid into the system 100 is thus implemented from an appropriate external source (not shown), configured as a pressurized vessel or a non-pressurized vessel, such as a Dewar vessel. Intake of compressed air into the system 100 is implemented via an air compressor, accordingly.

The system 100 further comprises a fluid intake pipe 14 with a first end positioned within the volatilization tank 13 and with a second end connected to an impeller arrangement 15. The fluid intake pipe 14 is thus configured to penetrate through the mixing tank 17 via two apertures located at the lower and the upper faces of the mixing tank, accordingly (in z-direction; see FIG. 2). The fluid intake pipe 14 may be positioned above the bottom of the volatilization tank 13 or directly in touch therewith; in the latter case the part of the fluid intake pipe 14 passing through the volatilization tank 13 comprises a number of wall apertures for fluid intake. The part of the fluid intake pipe 14 passing through the mixing tank 17 is configured without wall apertures.

Figure 2:
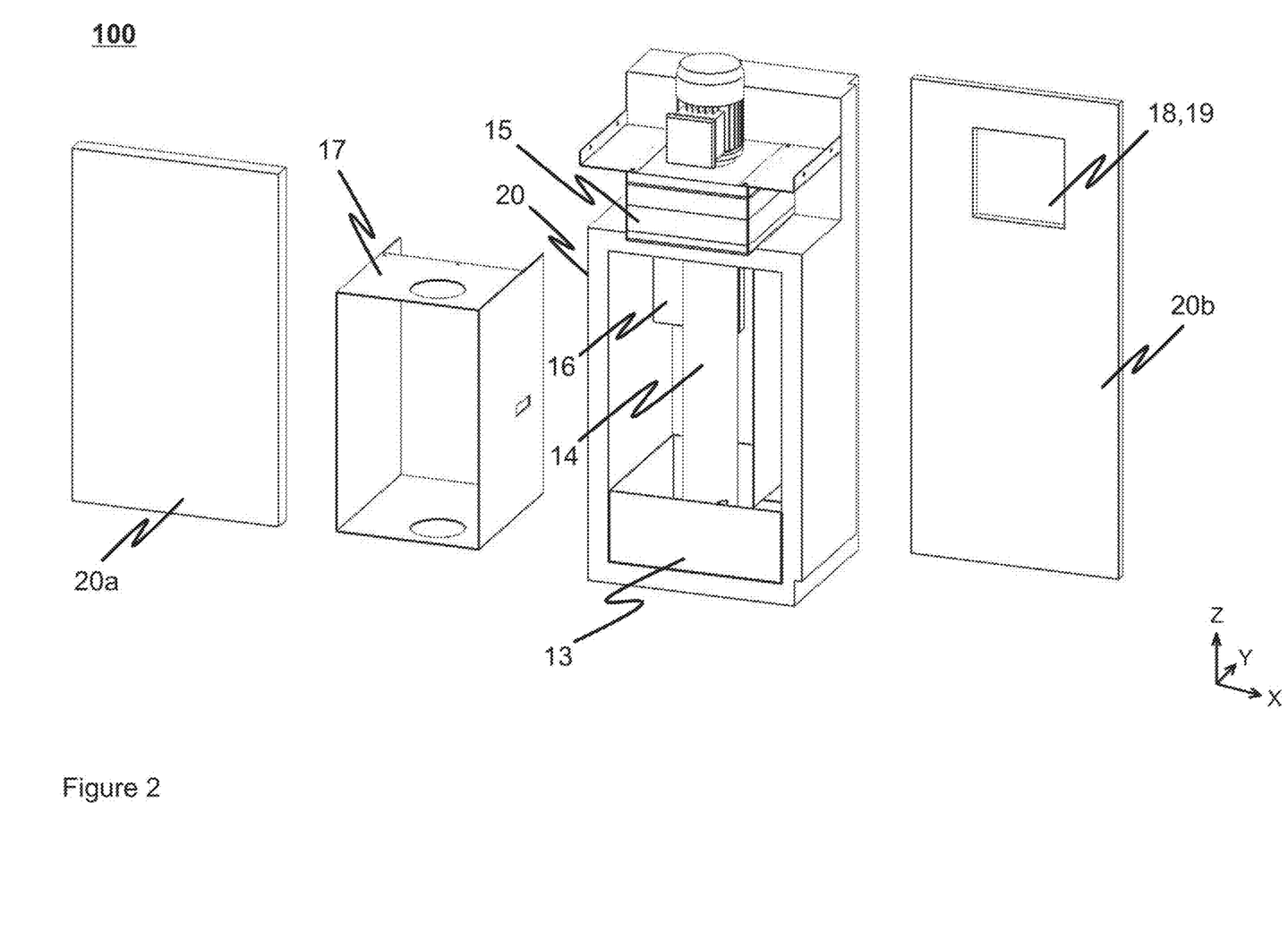
FIG. 2 shows a partially exploded view of the fluid circulation system of FIG. 1.

The system 100 further comprises a fluid return pipe 16 connected at a first end with the impeller arrangement 15 and with a second end entering the mixing tank 17 (FIGS. 1, 2).

Fluid communication between the system 100 and the patient cabin is implemented via inlet-outlet elements 18, 19. In one exemplary embodiment the back panel 20b of the casing 20 comprises an at least one aperture accommodating the elements' 18, 19 installation (FIG. 2).

Figure 3:
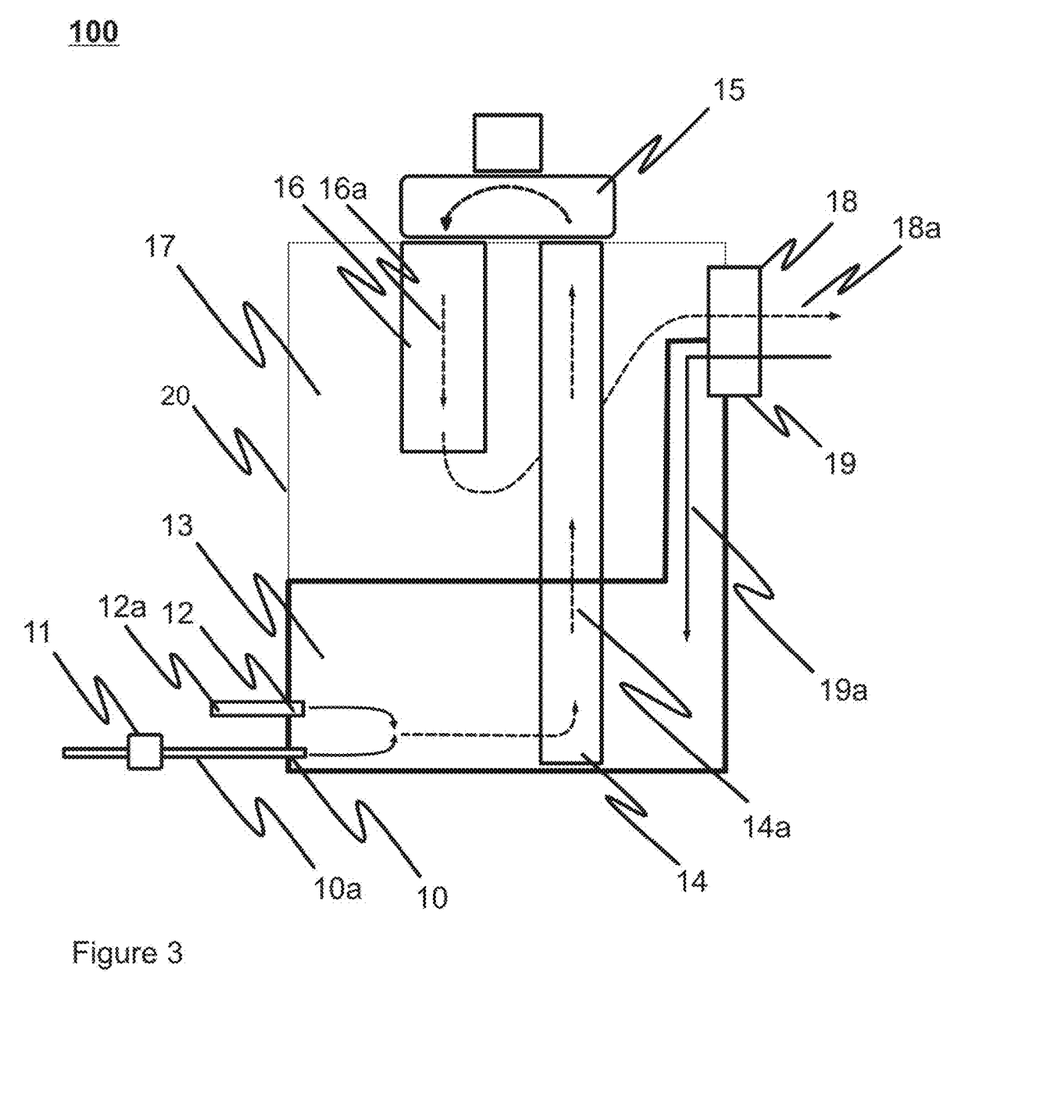
FIG. 3 is a block diagram of the fluid circulation system of FIG. 1, schematically illustrating circulation of fluids within said system.

FIG. 3 schematically illustrates an operating principle of the fluid circulation system 100. At the beginning of a cryotherapy session cryogenic liquid is supplied into the volatilization tank 13 via the cryogenic liquid intake appliance 12, 12a. To cope with the potential problems arising during the cryogenic liquid supply into the gas mixing/evaporation unit disclosed in the background section, the fluid circulation system 100 is configured to direct compressed air into the volatilization tank 13 via the intake appliance 10, 10a. Supply of compressed air is implemented simultaneously with that of cryogenic liquid and preferably in discontinuous, regular, periodic pulses (air bursts), wherein the control over an amount of supplied air, duration of each pulse (air burst) and time span therebetween is implemented via the least one control valve 11, preferably configured as a computer-regulated solenoid valve. Hence, by directing compressed air into the volatilization tank 13 in regular periodic pulses (air bursts), the cryogenic liquid present in said volatilization tank 13 is prevented from settling down on the bottom thereof. Intake appliances 10, 10a and 12, 12a are preferably located sidewise, adjacent to each other. According to the most preferred embodiment the compressed air supply intake appliance 10, 10a is arranged below the cryogenic liquid intake appliance 12, 12a. Such an arrangement creates conditions for a "forced" volatilization of cryogenic liquid that has entered the volatilization tank 13, thus promoting and/or intensifying volatilization of liquefied cold gas(es) in a most efficient manner. Moreover, upon such an accelerated and intensified volatilization of cryogenic liquid the temperature of ambient air present in the fluid circulation system 100 is reduced to the temperatures in a range of −100 to −180 degrees Celsius within a time period of 30-120 seconds. The cabin, accommodating a patient, can be further cooled down to the same temperatures in approximately the same time period.

Duration of each pulse (air burst) and time intervals therebetween may be adjusted for each individual cryotherapy session or at least partially standardized. Duration of each pulse may be adjusted within a range of 1-30 seconds, occurring in 5-60 seconds intervals, for example. Thus, for an exemplary 3 min cryotherapy session 5 sec air bursts may be scheduled within 10 sec intervals.

Supply of such air bursts into the volatilization tank 13 may proceed on a "background" of a continuous supply of cryogenic liquid. Alternatively, supply of cryogenic liquid may be implemented in batches.

Figure 4:
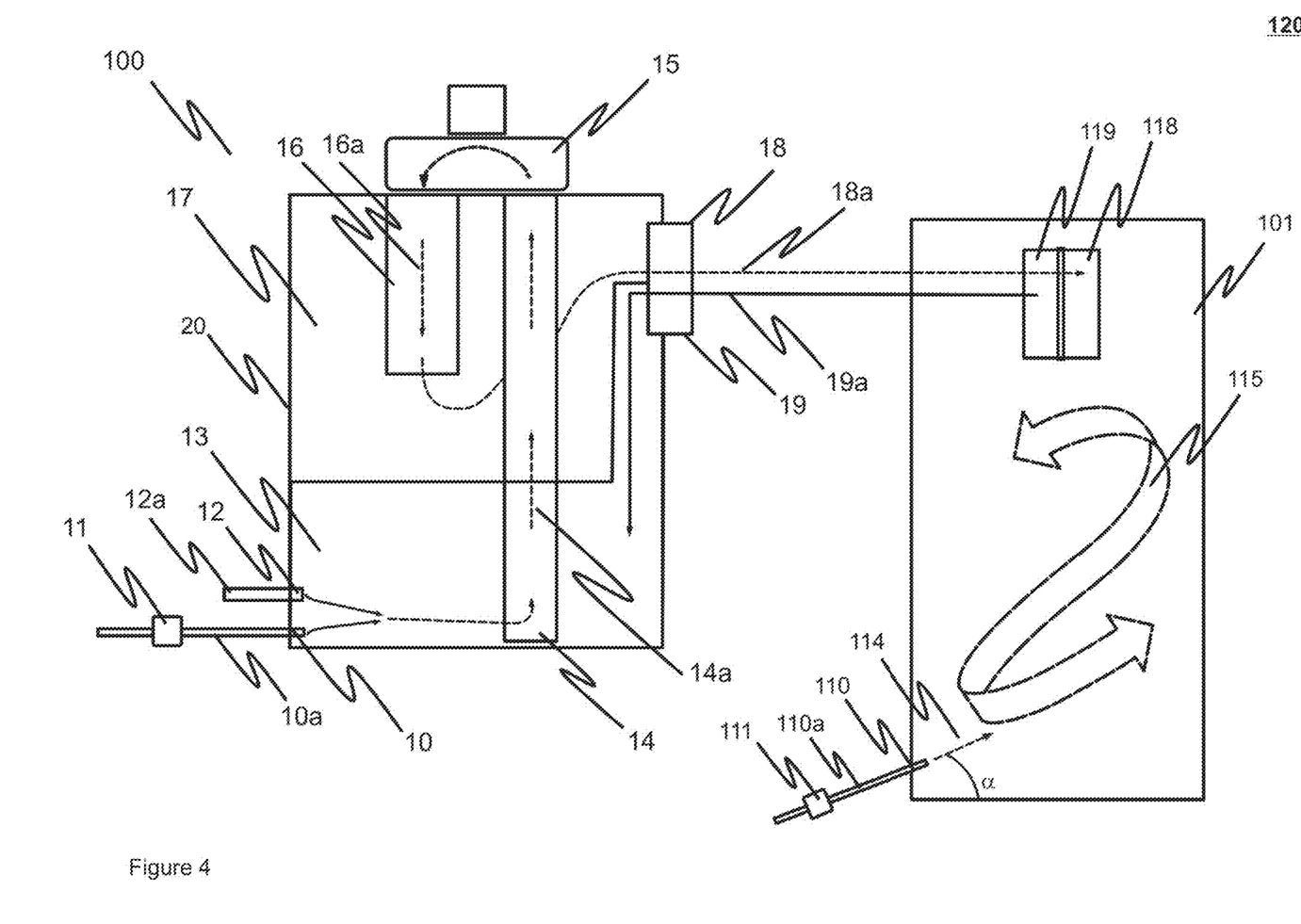
FIG. 4 is a block diagram of a cryocabin arrangement in accordance with another aspect of the invention, comprising the fluid circulation system of FIG. 1 and a cryogenic cabin for accommodating a patient.

Referring back to FIG. 3, cryogenic liquid is effectively mixed with air already in the volatilization tank 13. Thus created coolant mix is directed into the fluid intake pipe 14 by forces created by a rotating impeller within the impeller arrangement 15. By the term "coolant mix" we refer herewith to a mixture of cryogenic liquid (liquefied gas) and air, created upon blowing compressed air into the volatilization tank 13 containing said cryogenic liquid. In practice the coolant mix consists of air with volatilized cold gas(es) suspended therein. Coolant mix stream passing the fluid intake pipe 14 and entering the impeller arrangement 15 is indicated by a reference numeral 14a. Accordingly, from the impeller arrangement 15 the coolant mix is directed via a fluid return pipe 16, as 16a, into the mixing tank 17. In the mixing tank 17 the coolant mix is further mixed with ambient air and via the outlet 18 is directed, as 18a, into a cabin 101, suitable for accommodating a patient (FIG. 4). For clarity purposes the stream 18a will be referred herein below as a "cooling agent". The fluid intake pipe 14 and the fluid return pipe 16 thus form a pipe arrangement 14, 16.

The cabin 101 and the fluid circulation system 100 together form a cryocabin arrangement 120 for use in a whole-body cryotherapy treatment, according to the second aspect of the invention (FIG. 4). The cryocabin arrangement 120 is preferably implemented as that of a so-called "cryo-sauna" type, accordingly to the definition above. FIG. 4 also illustrates circulation of fluids within the cryocabin arrangement 120, as occurring between the fluid circulation system 100 and the cabin 101, as well as circulation of fluids occurring solely inside the cabin 101.

Hence, the cooling agent 18a, directed from the system 100 into the cabin 101 via the outlet 18, enters said cabin 101 via a cooling agent intake appliance 118, accordingly.

The cabin 101 is preferably configured as a vertical, shell-like chamber, open from the top and suitable for accommodating a standing adult person. Supply of the cooling agent into said cabin is implemented via the cooling agent intake appliance 118 disposed at the upper half of the cabin and comprising a number of jets, nozzles and/or any other appropriate means, equipped with protection shield(s). In one preferred embodiment the cabin 101 additionally comprises an at least one fluid supply port 110 for supply of compressed air inside the cabin, said at least one port 110 being connected, via an at least one corresponding intake line 110a, to the air compressor. The port 110 and the line 110a thus form a compressed air intake appliance 110, 110a for the cabin 101. The cabin 101 may be connected to the same air compressor equipment as the fluid circulation system 100, or, alternatively, to the separate air compressor equipment.

In one preferred embodiment supply of compressed air into the cabin 101 is implemented via discontinuous, regular, periodic pulses (air bursts), in the same manner as for the fluid circulation system 100, described above. Still, supply of compressed air into the cabin 101 may be also configured in a continuous manner. Control over an amount of compressed air supplied into the cabin 101 via the appliance 110, 110a, duration of each pulse (air burst) and time span therebetween is preferably implemented via an least one control valve 111, preferably configured as a computer-regulated solenoid valve.

In the most preferred embodiment the appliance 110, 110a is configured such, to establish a compressed air supply into the cabin 101 in an upward direction along a diagonally sloped line 114 (FIG. 4). The compressed air intake appliance 110, 110a is therefore positioned at the lower/bottom part of the cabin 101 within a sidewall thereof such, to create a diagonally ascending airstream 114. Preferred disposition of the appliance 110, 110a is therefore such, that the trajectory of compressed air stream 114 supplied into the cabin 101 forms an essentially acute inclination angle alpha ($\alpha$) with an imaginary line corresponding to the bottom of the cabin 101 (FIG. 4). The term "essentially acute angle" is used in the present disclosure to indicate an inclination angle formed between the trajectory of compressed air stream 114 blown into the cabin 101 and the bottom of said cabin being within a range of 1° to 89°, preferably within a range of 5° to 60°. Generation of diagonally ascending airstream 114 according to the aforesaid trajectory with an inclination angle less than 90° is essential for generating a vortex effect discussed further below.

Referring back to FIG. 4, upon the individual cryogenic treatment session the cooling agent 18a, is directed into the cabin 101 via the cooling agent intake appliance 118 located at the upper half thereof. By the "upper half" of the cabin 101 we refer to that part of the cabin located essentially above an imaginary middle point when measured along a vertical axis within the limits set by the height of the cabin 101. In order to prevent the cold gas(es), blown into the cabin 101 with the cooling agent 18a, from settling down at the bottom thereof, compressed air is guided diagonally upwards into the cabin 101 via the appliance 110, 110a, thereupon air pressure is also rising at the lower/bottom part of the cabin 101. Mixing together the cooling agent stream 18a blown from above (appliance 118) and the compressed air stream 114 blown diagonally upwards from below (appliance 110, 110a) result in generation of a fluidic whirl 115, referred herein below as a vortex phenomenon. Said fluidic whirl 115 can be further defined as a fluidic stream advancing upwards along a substantially circular or a spiral-like trajectory. At 115 the coolant agent stream 18a having a temperature within a range of −100 to −180 degrees Celsius encounters the ambient air stream 114 having a temperature within a range of above zero degrees Celsius (in practice, approximately 15-25 degrees Celsius). Aforementioned streams mix and, upon swirling, rise up due to an increased air pressure at the bottom of the cabin 101 to be further withdrawn therefrom via a fluid discharge appliance 119 located adjacent to the corresponding cooling agent intake appliance 118.

The cryocabin arrangement 120 is therefore configured, upon supply of the cooling agent stream 18a and the compressed air stream 114 into the cabin 101, to generate and maintain, during the course of the cryotherapy treatment session, a fluidic whirl 115 created upon interaction of aforesaid fluidic streams having distinct direction and temperature.

In preferred embodiment provision of the cryocabin arrangement 120 is such to ensure continuous fluid exchange between the cabin 101 and the fluid circulation system 100. Thus, discharge fluid being withdrawn from the cabin 101 via the fluid discharge appliance 119 is returned back into the fluid circulation system 100 via the corresponding inlet element 19. Returning, as 19a, discharge fluid enters directly the volatilization tank 13. The cryocabin arrangement 120 is therefore configured such that "intake" and "return" fluid communication paths therewithin are physically separated from each other. Thus, the cooling agent 18a, entering the cabin 101, is directed thereto via the mixing tank 17 of the system 100, whereas the discharge fluid 19a, being withdrawn from the cabin 101, is collected into the volatilization tank 13 of the system 100, accordingly.

Therefore, provision of both the cryocabin arrangement 120 and the fluid circulation system 100 enable continuous recirculation of fluids therewithin, wherein discharge fluid 19a returning from the cabin 101 is not discarded, but at least partially recycled as 14a (FIGS. 3, 4).

Referring back to FIGS. 3, 4, supply of compressed air into the volatilization tank 13 via the appliance 10, 10a thus mediates a double function within the fluid circulation system 100: promoting volatilization of cryogenic liquid, as discussed above and, additionally, effective mixing with discharge fluid stream 19a returning from the cabin 101, thus enabling continuous recirculation/recycling of fluids within the fluid circulation system 100 and the related cryocabin arrangement 120.

Figure 5:
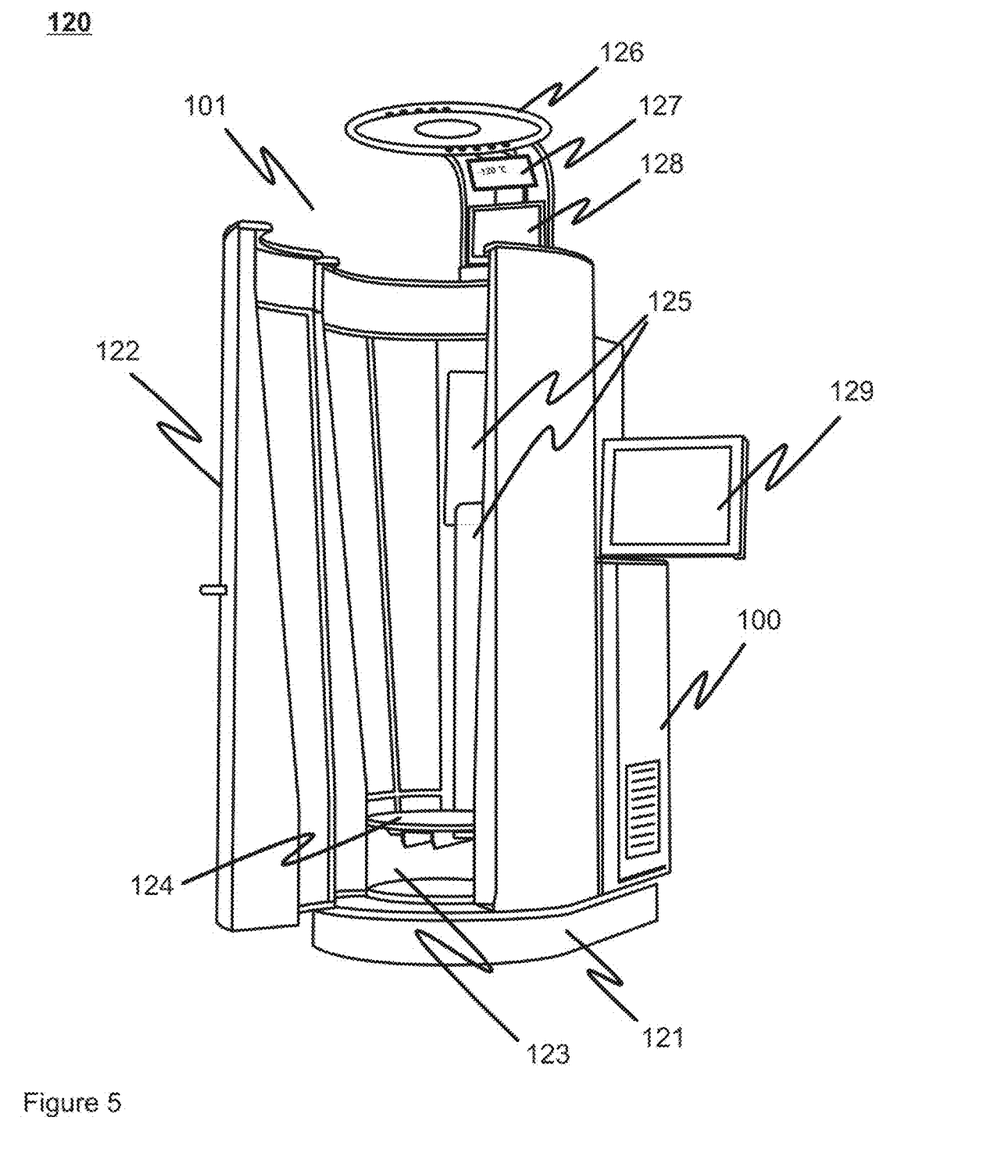
FIG. 5 shows a perspective view of the cryocabin arrangement of FIG. 4.

An exemplary embodiment of the cryocabin arrangement 120 is shown on FIG. 5. The cryocabin arrangement 120 thus comprises the cabin 101 and the fluid circulation system 100. The cabin 101 is configured in the form of a vertical open-top shell with a base 121, said shell configured to accommodate a standing adult person. The shell has a door 122, implemented as a hinged door (FIG. 5) or as a sliding door. The cabin 101 is thermally insulated. The cabin 101 further comprises a standing platform 124 disposed over the base 121 so that a space 123 is formed between the base 121 and the platform 124. The standing platform 124 may be configured height-adjustable in order to achieve best treatment results irrespectively of the patient's height; in such a case adjustment may be performed by moving the platform 124 along a vertical axis (up and down) within the limits set by the space 123. The cabin 101 is further equipped with protection shield(s) 125 positioned against the fluid intake appliances 118 and 110, 110a (aforesaid appliances not shown). The interior of the cabin 101 including protection shields 125 may be padded by a suitable cold-resisting material.

The cabin 101 is preferably configured to comprise a thermographic camera, comprising an at least one thermal sensor. Said sensor(s) may be infrared sensor(s); however, use of the sensor(s) based on any other suitable operation principle is not excluded. In one preferred embodiment the thermographic camera and/or the thermal sensor(s) may be integrated into a disc-shaped appliance 126, arranged at/connected to the upper border of the cabin 101. Additionally or alternatively the thermographic camera and/or the thermal sensor(s) may be integrated within the interior of the cabin 101. The thermographic camera and/or each thermal sensor are configured to measure a body temperature during the cryotherapy treatment session in real-time and optionally to generate a thermal map. Based on the readouts (the thermal map) provided by the thermographic camera, temperature within the cabin 101 may be adjusted individually for each patient by regulating compressed air intake thereto via the appliance 110, 110a (FIG. 4). Regulation may be implemented either manually or automatically; in the latter case regulation may be based on the temperature threshold data, for example.

Additionally or alternatively the appliance 126 may further comprise an at least one thermal sensor and an at least one image acquisition device in the form of distinct installations. The appliance 126 is preferably configured to further comprise a number of light/illumination sources, such as LEDs, for example.

The cabin 101 is further configured to comprise a number of sensors/detectors integrated into the interior thereof, for measuring inside the cabin external (i.e. patient unrelated) parameters, such as temperature, pressure, fluid flow and the like. Accordingly, the cabin 101 is further equipped with a number of parameter screens 127, 128. In one exemplary embodiment shown on FIG. 5 the parameter screen 127 is configured to show readouts from the detectors measuring the external (patient unrelated) parameters, including time, temperature and pressure measurements inside the cabin 101. The parameter screen 128 is, in turn, configured to show patient-related parameters, such as real-time readouts from the thermographic camera, for example.

In one preferred embodiment the cryocabin arrangement 120 further comprises a control terminal 129, equipped with a user interface. The user interface is realized as a graphical user interface in the form of a display screen, preferably a touchscreen. User interface may also comprise an at least one audio input-output device and an associated circuitry. The control terminal 129 is further provided with one or more processing devices containing a processing circuitry capable of interpreting and executing instructions input via the user interface, said processing devices being realized as microprocessors, microcontrollers, digital signal processors, programmable logic chips etc. The control terminal 129 is configured to acquire a direct electrical communication with each of the control valves 11, 111 regulating supply of compressed air into the fluid circulation system 100 and into the cabin 101, accordingly, and with the cryogenic liquid source, when the arrangement 120 is in operation. The control terminal 129 may be connected, in wired or wireless manner, to a central control terminal/processor (not shown) provided as a local—or remote computer, for example, including, but not limited to PC, portable or tablet computer, mobile phone, smart phone, PDA and the like.

Additionally, the cryocabin arrangement 120 comprises an ON/OFF switch for manual triggering the switch operation.

It is clear to a person skilled in the art that with the advancement of technology the basic ideas of the present invention may be implemented in various ways. The invention and its embodiments may generally vary within the scope of the appended claims.

The invention claimed is:

1. A fluid circulation system for a cryocabin used in a whole-body cryotherapy treatment and configured to supply a cooling agent directly into said cryocabin, said system comprising:

a volatilization tank and a mixing tank that are in fluid communication with each other and with the cryocabin, characterized in that said system further comprises a cryogenic liquid intake appliance formed by a port and a line for supply of cryogenic liquid into the volatilization tank and a compressed air intake appliance formed by a port and a line for supply of compressed air into the volatilization tank, said appliances disposed adjacent to each other, and in that said system is further configured for compressed air intake into the volatilization tank in regular periodic pulses during the course of the cryotherapy treatment session, wherein said system is configured to direct the cooling agent into the cryocabin via the mixing tank and to receive a discharge fluid from the cryocabin into the volatilization tank.

2. The fluid circulation system of claim 1, wherein the compressed air intake appliance is disposed below the cryogenic liquid intake appliance.

3. The fluid circulation system of claim 1, wherein intake of compressed air into the volatilization tank via the appliance is controlled by a computer-regulated valve, preferably a solenoid valve.

4. The fluid circulation system of claim 1, wherein the system is configured to direct a mixture of cryogenic liquid supplied via the appliance and air supplied via the appliance from the volatilization tank to the mixing tank via pipes and an impeller.

5. The fluid circulation system of claim 1, wherein cryogenic liquid supplied thereto is a mixture of liquid nitrogen and liquid oxygen, and wherein the content of liquid oxygen in said mixture is within a range of 19-21%.

6. The fluid circulation system of claim 1, wherein the system supplies into the cryocabin a cooling agent comprising volatilized cryogenic liquid and ambient air.

7. A cryocabin arrangement for use in a whole-body cryotherapy treatment, comprising a fluid circulation system according to claim 1 and a vertical open-top cabin for accommodating a patient.

* * * * *